(12) United States Patent
Feldman et al.

(10) Patent No.: US 11,495,340 B1
(45) Date of Patent: Nov. 8, 2022

(54) MEDICATION VENDING DEVICE HAVING MANUAL, AUTOMATIC, OR IMMEDIATE VENDING MODES FOR SELECTED SCHEDULED ADVANCE DOSE TIMES

(71) Applicant: Medherent, LLC, Annapolis, MD (US)

(72) Inventors: Joel F. Feldman, Owings Mills, MD (US); Yeardley W. Green, Stevenson, MD (US); Jeffrey C. Sweeter, Minnetonka, MN (US)

(73) Assignee: MEDHERENT, LLC, Annapolis, MD (US)

( * ) Notice: Subject to any disclaimer, the term of this patent is extended or adjusted under 35 U.S.C. 154(b) by 222 days.

(21) Appl. No.: 16/864,469

(22) Filed: May 1, 2020

(51) Int. Cl.
*G16H 20/13* (2018.01)
*G16H 40/40* (2018.01)

(52) U.S. Cl.
CPC ............. *G16H 20/13* (2018.01); *G16H 40/40* (2018.01)

(58) Field of Classification Search
CPC .............................. G16H 40/40; G16H 20/13
USPC .......................................................... 705/2, 3
See application file for complete search history.

(56) References Cited

U.S. PATENT DOCUMENTS

| | | | |
|---|---|---|---|
| 4,847,764 A | 7/1989 | Halvorson | |
| 5,752,235 A * | 5/1998 | Kehr | G08B 21/24 368/10 |
| 6,505,095 B1 | 1/2003 | Kolls | |
| 6,594,549 B2 | 7/2003 | Siegel | |
| 6,766,219 B1 | 7/2004 | Hasey | |
| 7,069,226 B1 | 6/2006 | Kleinfelter | |
| 7,264,136 B2 | 9/2007 | Willoughby et al. | |
| 7,574,377 B2 | 8/2009 | Carapelii | |
| 7,706,915 B2 | 4/2010 | Mohapatra et al. | |
| 7,963,201 B2 | 6/2011 | Willoughby et al. | |
| 8,019,471 B2 | 9/2011 | Bogash et al. | |

(Continued)

FOREIGN PATENT DOCUMENTS

WO WO-0163572 A1 * 8/2001 ............. G07F 11/54

OTHER PUBLICATIONS

Kassem, Abdallah; Antoun, Wissam; Hamad, Mustapha; El-Moucary, Chady; "A Comprehensive Approach for a Smart Medication Dispenser"; UOB Journals, 02 International Journal of Computing and Digital Systems, vol. 08, Issue 02; Mar. 1, 2019 (Year: 2019).*

(Continued)

*Primary Examiner* — Joshua B Blanchette
(74) *Attorney, Agent, or Firm* — Panitch Schwarze Belisario & Nadel LLP

(57) ABSTRACT

A medication vending device is provided with at least three distinct vending modes. A first vending mode causes the device to output a prompt at the respective dose time. The prompt communicates to the patient that a dose of medication should be vended from the device by the patient and immediately consumed. A second vending mode causes the device to automatically vend a dose of medication at the respective dose time without requiring any action by the patient. A third vending mode causes the device to immediately vend a dose of medication without requiring any action by the patient. The third vending mode allows for selection of a daily dose time from the plurality of daily dose times, and selection of one or more future dates, so as to cause immediate vending of the medication doses for the selected daily dose time for the selected one or more future dates.

14 Claims, 6 Drawing Sheets

(56) References Cited

U.S. PATENT DOCUMENTS

| | | | |
|---|---|---|---|
| 8,027,748 | B2 | 9/2011 | Handfield et al. |
| 8,090,472 | B2 | 1/2012 | Schifman et al. |
| 8,196,774 | B1 | 6/2012 | Clarke et al. |
| 8,467,897 | B2 | 6/2013 | Holmes et al. |
| 8,757,435 | B2 | 6/2014 | Van Oort et al. |
| 8,983,654 | B2 | 3/2015 | Sugimoto |
| 9,117,010 | B2 | 8/2015 | Feldman et al. |
| 9,477,817 | B2 | 10/2016 | Feldman et al. |
| 2001/0025208 | A1 | 9/2001 | Bartur |
| 2006/0200369 | A1 | 9/2006 | Batch et al. |
| 2009/0167531 | A1 | 7/2009 | Ferguson |
| 2009/0259486 | A1 | 10/2009 | Burg et al. |
| 2010/0114367 | A1 | 5/2010 | Barrett et al. |
| 2010/0168904 | A1 | 7/2010 | Henderson et al. |
| 2010/0305975 | A1 | 12/2010 | Daya et al. |
| 2010/0324936 | A1 | 12/2010 | Vishnubhatla et al. |
| 2011/0000170 | A1 | 1/2011 | Burg et al. |
| 2011/0193705 | A1* | 8/2011 | Sekura .................. A61J 7/04 340/573.1 |
| 2011/0202174 | A1 | 8/2011 | Bogash et al. |
| 2011/0251850 | A1 | 10/2011 | Stephens |
| 2015/0019009 | A1 | 1/2015 | Feldman et al. |
| 2017/0199966 | A1* | 7/2017 | Feldman ............ A61J 7/0481 |

OTHER PUBLICATIONS

Isabel Garcia, "Never Forget to Take Your Meds Again With This Pill-Dispensing Robot," Dec. 5, 2019 https://www.housebeautiful.com/lifestyle/a30139434/hero-pill-dispenser/&cd=11&hl=en&ct=clnk&gl=us (Year: 2019).*

"Data Transfer Standard EVA DTS 6.1" European Vending Association, Apr. 2008, 16 pages.

"EVA Data Transfer Standard." European Vending Association, printout from web page: http://www.vending-europe.eu/_includes/print.php?lg=en&cmp_id=17&safe_mode=, printout date: Feb. 29, 2012, original posting date: unknown, 3 pages.

"Notification of Transmittai of the International Search Report and the Written Opinion of the International Searching Authority . . . " and corresponding "Search History" document for PCT/US14/30316, dated Mar. 16, 2015, 26 pages.

Brochure for PointClickCare eMAR system. Printout from web page: https://www.pointclickcare.com/pccwebsite/pdfs/eMar_VicVillage.pdf, 2008, 2 pages.

Extended European Search Report dated Oct. 21, 2016 in EP Application No. 14765513.8.

Gene Ostendorf, "DEX and MDB: A Primer for Vendors." printout from web page: http://www.vendingmarketwatch.com/article/10272928/dex-and-mdb-a-primer-for-vendors, Feb. 7, 2008, 5 pages.

International Preliminary Report on Patentability for PCT/US14/30316, dated Sep. 24, 2015, 12 pages.

JuGeon Pak and KeeHyun Park. "Construction of a smart medication dispenser with a high degree of scalability and remote manageability." Journal of Biomedicine and Biotechnology, 2012, 10 pages.

Karla Miller et al., "Evaluation of medications removed from automated dispensing machines using the override function leading to multiple system changes," printout from web page: http://www.ahrq.gov/downloads/pub/advances2/vol4/Advances-Miller_93.pdf, original publication date: 2008 (as per Internet Archive Wayback Machine records), 7 pages.

Michael L. Kasavana and Glenn Butler, "Vending Technology Revolution." printout from web page: http://www.vending.org/technology/Vending_Technology_Revolution.pdf, original publication date: 2010 (as per Internet Archive Wayback Machine records), 11 pages.

Office Action dated Aug. 11, 2016 in Canadian Patent Application No. 2,906,161, 8 pages.

Office Action dated Feb. 9, 2017 in Canadian Patent Application No. 2,906,161, 8 pages.

Office Action dated Aug. 8, 2017 in CA Application No. 2,906,161.

PCT Invitation to Pay Additional Fees and Where Applicable, Protest Fees for PCT/US14/30316 dated Jan. 15, 2015, 3 pages.

Product brochure for "MedSupport® for Providers." CaraSolva, Inc., Boulder, Colorado, 2011, 2 pages.

Product brochure for "MedSupport®." CaraSolva, Inc., Boulder, Colorado, 2011, 2 pages.

Product brochure for "PharmacySupport." CaraSolva, Inc., Boulder, Colorado, 2011, 2 pages.

Rajeev B. Patel, "Reduction in Medication Errors in Hospitals." printout from web page: http://www.cwru.edu/med/epidbio/mphp439/Reduction%20in%20Medication%20Errors%20in%20Hospitals.htm, Spring 2004, 11 pages.

Wikipedia entry for "Health Level 7." printout from: http://en.wikipedia.org/wiki/Health_Level_7, last modified date: Dec. 28, 2011, 11 pages.

Wkipedia entry for "Medication Administration Record." printout from web page: http://en.wikipedia.org/wiki/Medication_Administration_Record, last modified date: Dec. 23, 2011, 2 pages.

* cited by examiner

Example of a scheduled dose time
(Schedule checkbox checked)

☐ 8 PM

Example of an unscheduled dose time
(Schedule uncheckbox checked)

☐ 8 PM

Example of immediate dispensing
(Vending)

Online
Last Check In: 6/26/2019 09:35 AM

Today's Doses

| 08:00 AM | Dispensed | 100% | 7 |
| 10:00 AM | Queued | 100% | 8 |
| 12:00 PM | Queued | 100% | 8 |
| 02:00 PM | Queued | 100% | 8 |

S Kelly

| ADS | Remote Control | Door Events | Power Events | Table Data | Notes | Logs |

Advance Dose Scheduler   01/1/2020   To   013/1/2020   Edit

Fred Rogers

Wed, Jan 8 2020   4 PM  Dispensed
                  8 PM  Cancelled

Wed, Jan 8 2020   4 PM  Queued
                  8 PM  Queued

Wed, Jan 8 2020   12 PM  Queued

Close

*Figure 6*

MEDICATION VENDING DEVICE HAVING MANUAL, AUTOMATIC, OR IMMEDIATE VENDING MODES FOR SELECTED SCHEDULED ADVANCE DOSE TIMES

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

Medication vending or dispensing devices (collectively referred to hereafter as "medication vending devices") which vend medications in accordance with a preprogrammed medication dosing schedule generally fall into two different categories with respect to their vending or dispensing functionalities. Medication dosing schedules indicate which medications should be taken at different dose times of the day. Dosing schedules are typically the same each day, but some dosing schedules may require multiple days to define a proper schedule, especially when a particular medication is not taken every day of a given week, or is taken at different dose levels or dose times on different days of a given week.

The first category of medication vending devices output a prompt when a dosing time occurs. The prompt indicates that the patient should take action to cause the medication vending device to release the appropriate medication therefrom which is associated with the current dose time so that the medication can be immediately consumed. In some cases, a PIN , must be entered by the patient or a caregiver to complete the vending process. One example of this type of medication vending device is described in U.S. Pat. No. 9,117,010 (Feldman et al.), which is incorporated by reference herein.

The second category of medication vending devices are automatically programmed to vend all medication doses at their respective scheduled dose times, without requiring any patient action. Such devices may also prompt the patient to immediately consume the vended medication.

The medication vending device described in U.S. Pat. No. 9,117,010 also has a mode, referred to as an "Away Mode," that allows for selected doses to be vended in advance of when the dose scheduling is set. When using the "Away Mode," the user enters a date range in the future and all doses that are scheduled to occur within that date range are immediately vended from the device. Consider the following example:

1. A patient's caregiver vends medications from the device for the patient at each dose time. In this particular example, a PIN must be entered by the caregiver, and confirmed by the device, before each medication dose can be released from the device.

2. The caregiver will be unavailable for an upcoming period of time due to a planned vacation, medical leave, or the like. However, the patient can be entrusted to take the medication doses on their own accord during the caregiver's absence, or the caregiver has made an alternative arrangement for another caretaker to be present during their time of absence. For security and patient health and safety reasons, the patient does not know the PIN, and the caregiver does not wish to provide the patient with the PIN.

3. The dosing schedule is set to vend medications three times a day, at 8:00 am, 12:00 noon, and 6:00 pm.

4. The current date/time is Monday, Jun. 15, 2020 at 12:00 noon.

3. A date range (time window) is entered for the time period where the caregiver will be absent, such as Thursday, June 18 through Saturday, June 20. The PIN is also entered.

4. The device immediately vends all of the medication doses scheduled for the date range (time window), which totals nine medication doses.

5. The caretaker then gives the medication doses to the patient or to the alternative caretaker, with instructions on when the respective medication doses should be taken.

The combination of vending modes in the medication vending device described in U.S. Pat. No. 9,117,010, namely, a default mode that issues a prompt when a dosing time occurs, and the above-described "Away Mode," lack flexibility for a wide range of scenarios that are faced in the real-world. The medication vending devices that are automatically programmed to vend all medication doses at their respective scheduled dose times, without requiring any patient action, are similarly inflexible.

Thus, there is a need for a medication vending device that has more robust and granular vending modes. The present invention fulfills such a need.

SUMMARY OF THE PRESENT INVENTION

A medication vending device is provided with at least three distinct vending modes. A first vending mode causes the device to output a prompt at the respective dose time. The prompt communicates to the patient that a dose of medication should be vended from the device by the patient and immediately consumed. A second vending mode causes the device to automatically vend a dose of medication at the respective dose time without requiring any action by the patient. A third vending mode causes the device to immediately vend a dose of medication without requiring any action by the patient. The third vending mode allows for selection of a daily dose time from the plurality of daily dose times, and selection of one or more future dates, so as to cause immediate vending of the medication doses for the selected daily dose time for the selected one or more future dates.

BRIEF DESCRIPTION OF THE DRAWINGS

Preferred embodiments of the present invention will now be described by way of example with reference to the accompanying drawings:

FIGS. 2-6 show portions of user interface display screens for implementing the system of FIG. 1.

DETAILED DESCRIPTION OF THE INVENTION

Figure 1:
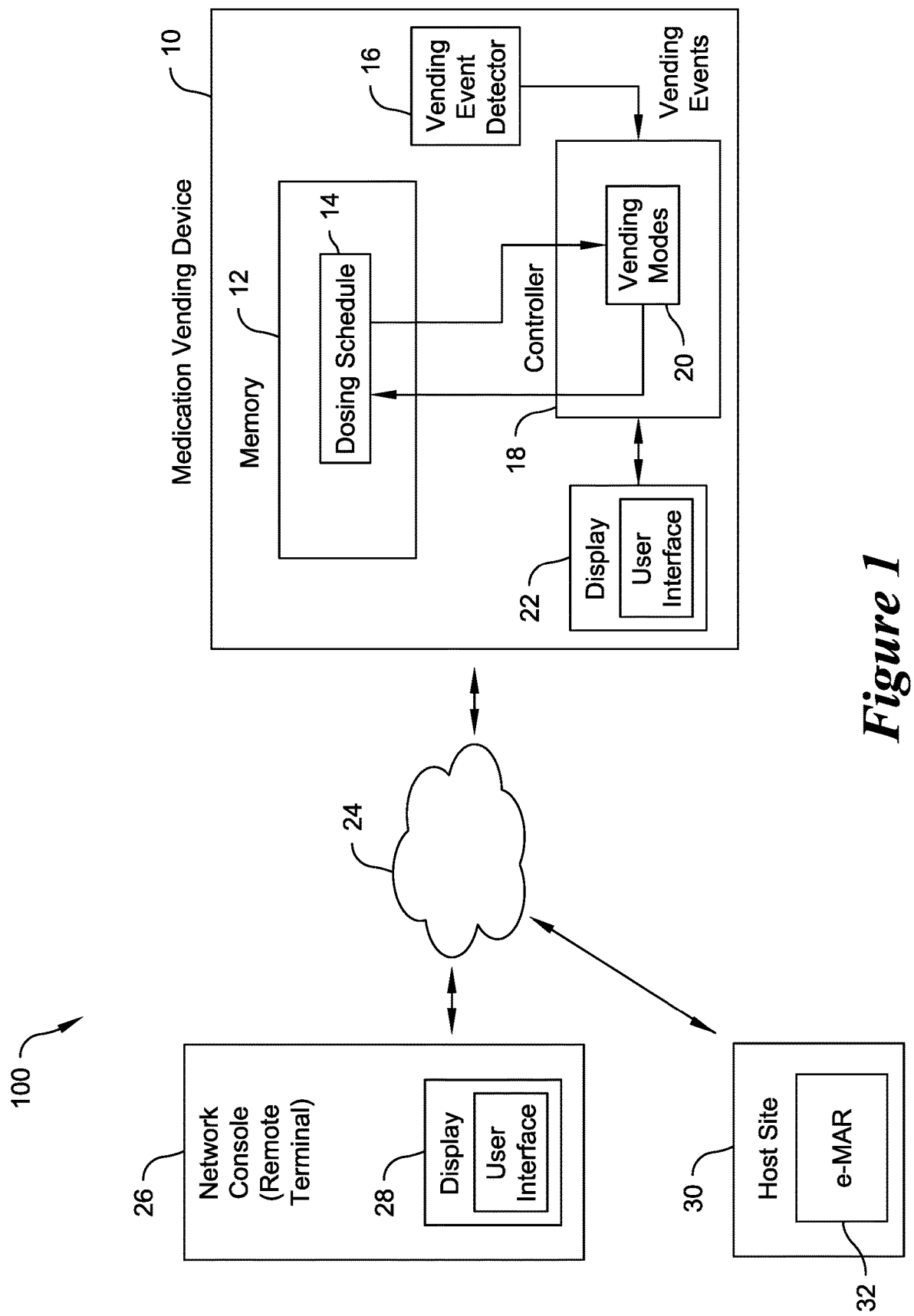
FIG. 1 is a schematic diagram of a system that integrates a medication vending device with remote control and monitoring elements, in accordance with one preferred embodiment of the present invention.

Certain terminology is used herein for convenience only and is not to be taken as a limitation on the present invention.

The words "a" and "an", as used in the claims and in the corresponding portions of the specification, mean "at least one."

This patent application includes an Appendix having a file named appendix688372-22US.txt, created on Apr. 23, 2020, and having a size of 38,839 bytes. The Appendix is incorporated by reference into the present patent application. One preferred embodiment of the present invention is implemented via the source code in the Appendix. The Appendix is subject to the "Copyright Notice and Authorization" stated above.

The present invention may be used to track the ingestion/administering/vending of single medicine packages or Multi-Unit Dose Packages or Multi-Unit Drug Packages (MUDPs). An MUDP contains one dosage of medicines that are prescribed for a specific treatment regimen. That is, there are a plurality of different medicines in an MUDP, and there may be one or pills of each medicine to obtain the desired dosage. All of the different medications in an MUDP packet are meant to be taken at the same time. MUDPs are typically created using specialized robotic machinery. However, the scope of the present invention includes MUDPs that are manually packaged in simple plastic packets or the like.

An MUDP typically includes a label that describes its contents, or it may include human or machine readable indicia (e.g., an ID number) that functions as a pointer in a database memory that stores its contents. The label may also include patient identifying information. The machine readable indicia may be a bar code or QR code that identifies the patient, date, and medication. The examples described below relate to MUDPs, but the scope of the present invention includes single medicines or packages that include only one medicine type per package.

Dispensing vs. Vending: As discussed in U.S. Pat. No. 9,117,010, there are two steps involved in the medication lifecycle. The first step in the lifecycle is a dispensing step which occurs when a pharmacist or similarly qualified individual fills a medication vending device, such as the one described in the present invention, with proscribed medications. This step is conventionally referred to as "medication dispensing," wherein specific medication(s) are delivered to a patient in fulfillment of a prescription. Typically, the medications are physically handed to the patient, but in the present invention, the medications are loaded into the medication vending device, thereby completing the dispensing step. The second step in the lifecycle is a vending step wherein the medication vending device releases the previously dispensed medications to the patient. In a conventional vending machine, the release of a product from a vending machine is typically referred to as a dispensing event, but in the context of the present invention, it is referred to as vending event, because the dispensing event occurred when the medication vending device was loaded with the medications. While dispensing and vending are different steps in the medication lifecycle, the discussion below uses these terms interchangeably. Thus, for purposes of the present invention, all references below to "dispensing" and permutations thereof are deemed to be equivalent to the act of "vending" (a vending event).

Between the first and second steps of the medication lifecycle, additional actions (intermediary steps) occur. One intermediary step is that the dispensed medications are provided to a technician who physically loads the medications into the medication vending device. Another intermediary step is that the dispensed medications are packaged into single medicine packages or MUDPs, as discussed above. The packaging occurs prior to the step of the technician loading the medication vending device.

Dosing schedule: A patient's dosing schedule is similar to the dose schedule shown for Patient ID 1234 in FIG. 43 of U.S. Pat. No. 9,117,010, repeated below for convenience.

TABLE 1

| Dosing schedule | Dispensed meds (meds that are scheduled to be dispensed and which were previously placed in the vending machine) |
| --- | --- |
| 8:00 am | 1 pill of MEDICINE A |
| | 1 pill of MEDICINE B |
| | 2 pills of MEDICINE C |
| 12:00 noon | 1 pill of MEDICINE D |
| | 1 pill of MEDICINE E |
| 8:00 pm | 1 pill of MEDICINE A |
| | 1 pill of MEDICINE B |
| | 2 pills of MEDICINE C |

In this example, the medications are vended in multi-unit dose packages (MUDPs). Thus, a single package contains all of the medications vended at a respective dose time. This example relates to MUDPs, but the scope of the present invention includes single non-packaged medicines, or packages that include only one medicine type per package.

I. Overview

FIG. 1 is a schematic diagram of a system 100 in accordance with one preferred embodiment of the present invention. The system 100 includes a plurality of medication vending devices 10 (only one such device 10 is shown in FIG. 1), a plurality of network consoles (remote terminals) 26 (only one such network console 26 is shown in FIG. 1), and host site 30.

One example of the medication vending device 10 may be the device described in U.S. Pat. No. 9,117,010, enhanced with the features described below regarding new vending modes. In the preferred embodiment, the medication vending device 10 does not include the "Away Mode" in the device described in U.S. Pat. No. 9,117,010. The medication vending device 10 is associated with a patient using any of the identifying techniques described in U.S. Pat. No. 9,117,010.

The medication vending device 10 includes memory 12 that stores a dosing schedule 14 for medication doses that are loaded into the medical vending device 10. The dosing schedule includes (i) a plurality of dose (dosing) times per day, each day including a fixed number of dose times, and (ii) medications that are scheduled to be vended at each dose time.

The medication vending device 10 also includes a vending event detector 16 that outputs a vending event signal when medication is released from the medication vending device 10.

The medication vending device 10 further includes a controller 18 configured to perform the following functions:

i. Generate an electronic message whenever a vending event occurs at the medication vending device 10. As noted above, the medication vending device 10 includes the vending event detector 16 that detects such events.

ii. Program each dose time with a respective, vending mode 20. The vending modes, 20 include at least the following three vending modes:

First vending mode: This vending mode is configured to cause the medication vending device 10 to output a prompt at the respective dose time. The prompt communicates to the patient that a dose of medication should he vended from the medication vending device 10 by the patient, or the patient's caregiver, and immediately consumed. Vending occurs by pressing a button on the medication vending device 10, or by using an equivalent input means. Voice command may also be used. In one preferred embodiment, the first vending mode is a default mode, meaning that unless a different vending mode is selected, the vending mode for a particular dose time defaults to the first vending mode. In one embodiment, a PIN must be entered by the patient or a caregiver to complete the vending process.

Second vending mode: This vending mode causes the medication vending device 10 to automatically vend a dose of medication from the medication vending device 10 at the respective dose time without requiring any action by the patient. For this vending mode, the medication vending device 10 preferably communicates to the patient that the automatically vended dose of medication vended from the medication vending device 10 should be immediately consumed.

Third vending mode: This vending mode causes the medication vending device 10 to immediately vend a dose of medication from the medication vending device 10 without requiring any action by the patient The third vending mode is configured to allow for:
 (A) selection of a daily dose time from the plurality of daily dose times, and
 (B) selection of one or more future dates, so as to cause immediate vending of the medication doses for the selected daily dose time for the selected one or more future dates.

In one preferred embodiment, the third vending mode is configured to allow for selection of a plurality of future dates, so as to cause immediate vending of the medication doses for the selected daily dose time for the selected plurality of future dates. The plurality of future dates may be consecutive or non-consecutive future dates (e.g., 12:00 noon and 6:00 pm dose for upcoming Monday-Friday; or 12:00 noon and 6:00 pm dose for upcoming Monday, Wednesday, Friday).

In another preferred embodiment, the third vending mode is configured to allow for:
 (A) selection of only one of the daily dose times from the plurality of daily dose times, and
 (B) selection of one or more future dates, so as to cause immediate vending of the medication doses for the one selected daily dose time for the selected one or more future dates (e.g., only the 12:00 noon dose for upcoming Monday-Friday; only the 12:00 noon dose for upcoming Monday, Wednesday, Friday).

The medication vending device 10 also includes a user interface (UI) display 22.

The medication vending device 10 is in electronic communication via wired or wireless electronic network 24 with one of the network consoles (remote terminals) 26. The electronic network 24 may be the internet, ethernet, WAN/LAN, or the like. The network console 26 includes user interface display 28. As discussed below, programming of the vending modes 20 of the controller 18 may occur using either the internal user interface display 22, or the external user interface display 26 of the network console 26, depending upon how an administrator has configured the overall system.

The medication vending device 10 is also in electronic communication via the wired or wireless electronic network 24 with the host site 30 that maintains an electronic medication administration record (e-MAR or eMAR) 32 for maintaining records of vended medications based on vending event signals generated by the vending event detector 16 of the medication vending device 10, in a manner similar to the host site and e-MAR shown in FIG. 1 of U.S. Pat. No. 9,117,010. In use, there are a plurality of medication vending devices 10 at different patient-based locations, each device being associated with a different patient, and the e-MAR 32 tracks the vending status of the plurality of patients.

The following examples illustrate scenarios that take advantage of the plurality of vending modes described above.

Example 1

A patient's dosing schedule requires taking medications three times per day, namely, at 8:00 am (morning dose), 12:00 noon, and 6:00 pm (evening dose). A patient's caregiver normally vends medications from the device for the patient at each dose time. A PIN must be entered by the caregiver, and confirmed by the device, before each medication dose can be released from the device. The caregiver will be unavailable to provide the patient with their 12:00 noon medication dose two days from now due to an obligation that the caregiver has that day. For any number of reasons, such as patient safety or patient security, the patient cannot be provided with the PIN.

The caregiver reprograms the controller to set the 12:00 noon medication dose two days from now from its current default first vending mode to the second vending mode, thereby allowing the medication vending device to automatically vend the 12:00 noon medication dose without requiring any action by the patient or the caregiver, other than to remove the medication dose from the dispensing tray and consume the medication.

The prior art "Away Mode" did not have the flexibility to granularly select individual medication dose times, and thus could not accommodate the scenario described above.

Example 2

A patient's caregiver normally vends medications from the device for the patient at the morning and evening dose time. A PIN must be entered by the caregiver, and confirmed by the device, before each medication dose can be released from the device. The medication vending device is located at the patient's residence (home location).

At the time of the morning and evening medication doses, the patient and their caregiver are both normally located at patient's home location, and the caregiver can give the medication doses to the patient each morning and evening. However, during most weekdays, the patient is at a different location (daytime location/facility), such as a location/facility that provides for activities and/or therapy. Thus, the patient is not in their home environment when the 12:00 noon medication dose should be taken. The caregiver may also be with the patient at the daytime location/facility, or the patient may be with a different caregiver at the daytime location/facility. The caregiver at the daytime location/facility is thus responsible for providing the patient with the 12:00 noon medication dose.

To facilitate this arrangement, each week (e.g., during the weekend, or on Monday morning), the caregiver reprograms the controller to immediately vend the 12:00 noon medication doses for the upcoming weekdays (Monday-Friday). This is accomplished by changing the current default first vending mode to the third vending mode for the upcoming weekdays. The caregiver takes the five medication doses to the daytime location/facility. The caregiver at the daytime location/facility then provides them to the patient, one per day, at 12:00 noon. This reprogramming affects only the 12:00 noon medication doses for the upcoming weekdays.

Again, the prior art "Away Mode" did not have the flexibility to granularly select individual medication dose times, and thus could not accommodate the scenario described above.

II. Detailed Disclosure of Preferred Embodiments

As background to the detailed disclosure, the following terminology is used:

Dispense: means the same as "vend," as discussed above.

Advance Dose Scheduler (ADS): name given for the flexible scheduling system that includes the three vending modes described above.

Away button: This is a button on the prior art medication vending device that was used for "Away Mode" programming. As described below, the button has been repurposed to initiate the new vending modes.

Standard dispense: This means that a prompt will be provided by the medication vending device 10 to remind the patient to release the current medication dose from the device for immediate consumption. This is equivalent to the first vending mode described above.

Scheduled: This means that the medication dose is set to automatically dispense (vend) at the scheduled time of the medication dose. This is equivalent to the second vending mode described above.

Dispense now: This means that the medication dose will be immediately dispensed (vended). This is equivalent to the third vending mode.

Figure 2:
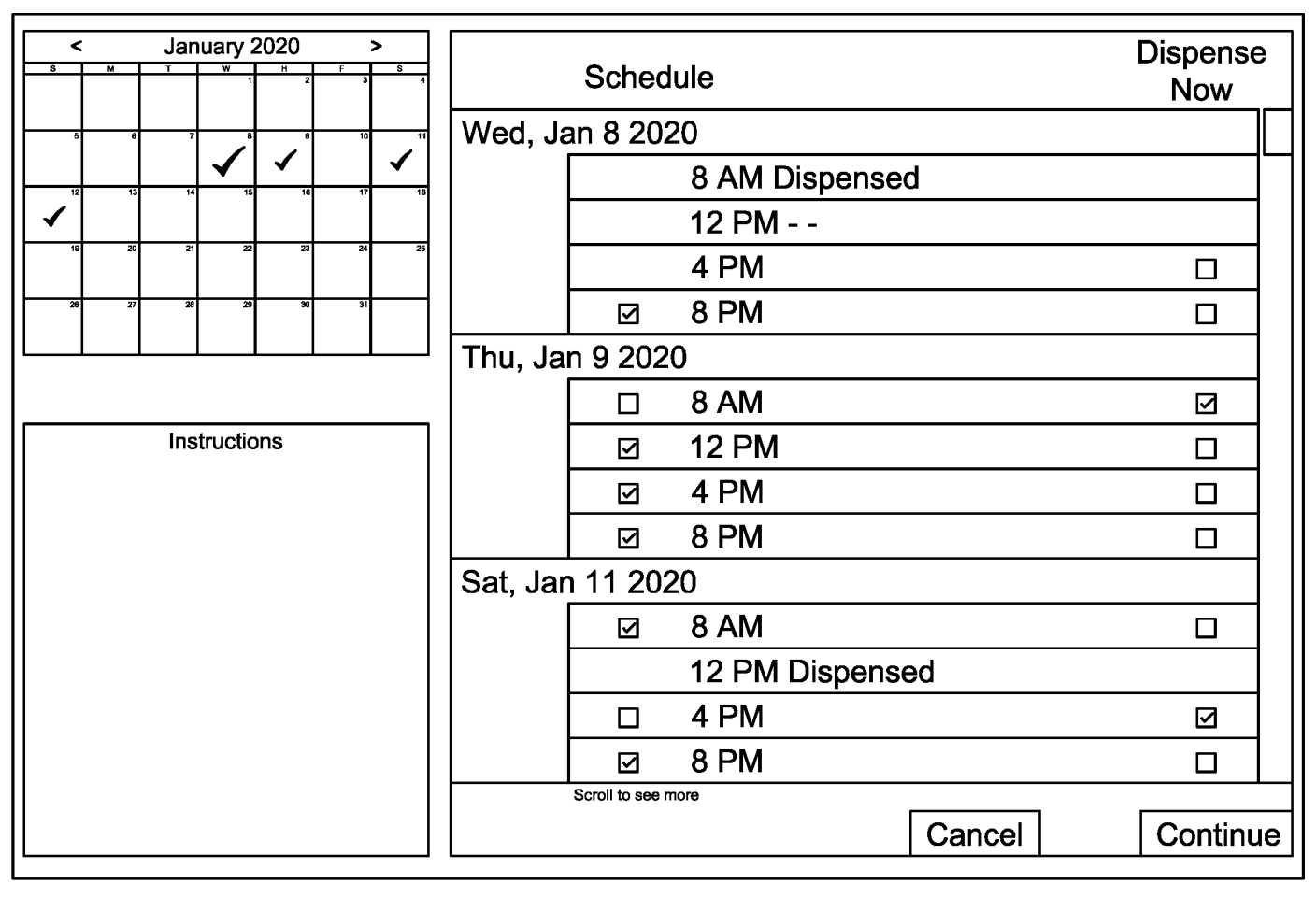

FIG. 2 is a user interface display for use in programming the various vending modes. The user interface display may be associated with the user interface display 22 of the medication vending device 10, or the user interface display 28 associated with the network console 26.

The ADS provides a user interface for scheduling advance doses in both the device controller 18 and the network console 26. The ADS is accessed via an "Away" button on the home screen of the user interface. The user interface presents the user with the current ADS scheduled items in chronological order along with a calendar view for high-level oversight. The home screen Away button displays a calendar icon whenever there are scheduled advance doses.

The following instructions appear below the calendar in FIG. 2:

BEGINNING OF INSTRUCTIONS

Days with checkmarks have scheduled doses.

Select days by tapping them. Doses for selected days are displayed in the list grouped by date. Selected days contain a checkmark.

Select each dose time in the list to either schedule or dispense now by checking the respective checkbox.

Tap Continue to schedule/dispense selections or Cancel to exit without changes.

END OF INSTRUCTIONS

When user taps on the Away button from the home screen with proper security rights, a new screen will be displayed that shows a new custom calendar view, an instruction guide, and a list of existing scheduled advance doses.

The custom calendar view defaults to the current month/year and highlights the current day (here, January 8 at 4:23 PM). Days with scheduled advance dose times display a checkmark. The month and year can be changed one month at a time using the navigation buttons on either side of the month/year label.

To the right of the calendar is a list of dose times grouped by the respective days selected (checked) in the calendar view. The list may also contain days selected in months other than the current calendar month displayed. Checked dose times are scheduled, or will be scheduled when the user continues on. Unchecked dose times will not be scheduled, or will be removed from schedule respectively.

FIG. 3 shows a portion of the user interface display screen for three different examples of how to program a particular dose time. The order of the illustrated vending modes is the second, first and third vending modes, respectively. Regarding the third vending mode example, the user has the option of dispensing discrete dose times immediately rather than scheduling them. This is done by checking the Dispense Now (right side) checkboxes for the respective discrete dose times. Dispense Now and Schedule checkboxes are mutually exclusive, so only either of one can be checked. These checkboxes cannot be simultaneously checked for the same dose time and date.

If the user taps continue in FIG. 2, the selections will be calculated accordingly against current logical inventory. If there is a shortfall, the user will be prompted with the affected dose times, for both scheduling and dispensing immediately.

Figure 4:
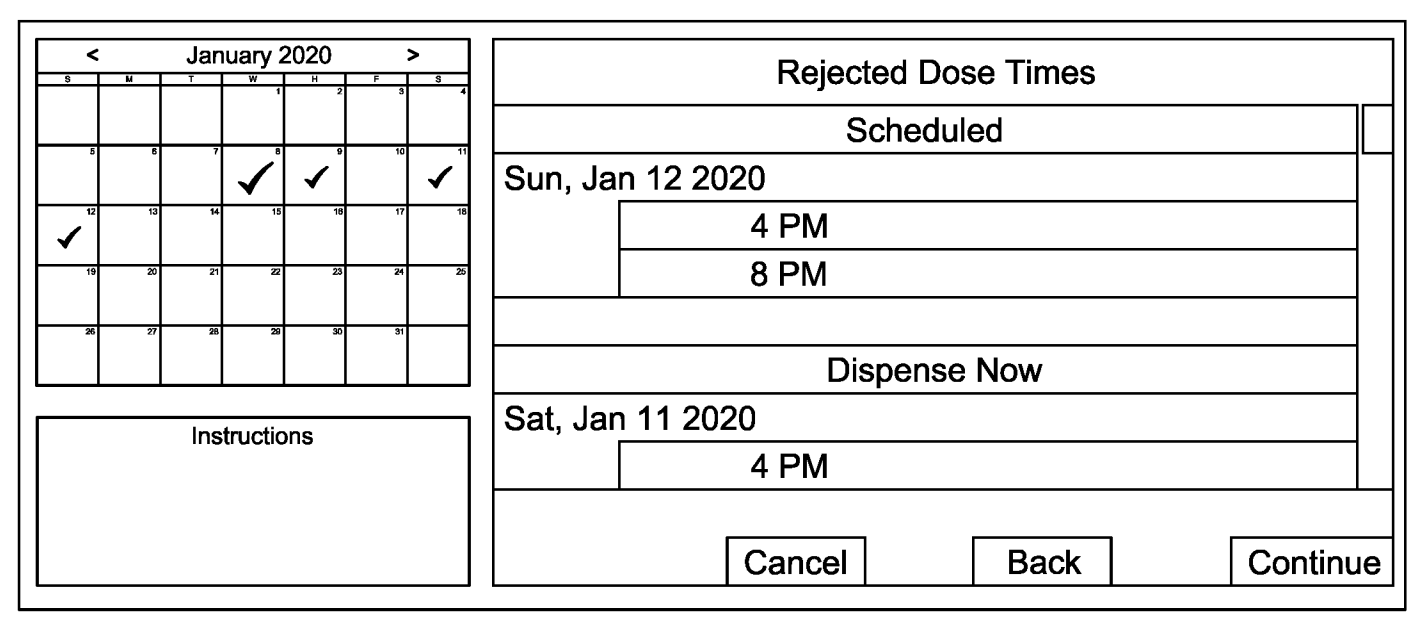

FIG. 4 is a user interface display that appears when or if there is an inventory shortfall.

The following instructions appear below the calendar in FIG. 4:

BEGINNING OF INSTRUCTIONS

Checked days have scheduled doses or dispenses.

There is insufficient inventory.

END OF INSTRUCTIONS

When determining inventory sufficiency, priority is given to nearer term doses, and assumes regular dispensing under normal operations for unscheduled doses. Further out future doses get "rejected" from schedule or immediate dispensing when inventory is insufficient. The user is prompted when this occurs for action to continue on with rejections omitted, back to adjust selections, or cancel to dismiss changes altogether.

The example situation illustrated above is such (where some schedule items are not shown to illustrate scroll):

Wed., January 8
   8 AM—Dispensed
   12 PM—In Past
   4 PM—Standard dispense
   8 PM—Scheduled Thu., January 9
   8 AM—Dispense now
   12 PM—Scheduled
   4 PM—Scheduled
   8 PM—Scheduled Fri., January 10
   8 AM—Standard dispense
   12 PM—Standard dispense
   4 PM—Standard dispense
   8 PM—Standard dispense Sat., January 11
   8 AM—Scheduled
   12 PM—Scheduled
   4 PM—Dispense now
   8 PM—Scheduled Sun., January 12
   8 AM—Scheduled
   12 PM—Scheduled
   4 PM—Scheduled
   8 PM—Scheduled
In this example. the current inventory levels are:
8 AM—4
12 PM—4
4 PM—3
8 PM—4

The current logical inventory will not support dispensing for the immediate or scheduled dispenses and still meet the interim demands for dose times 4 PM and 8 PM where a minimum inventory of 5 is needed to meet sufficient demand for each respectively through Sun., January 12. An assumption is that dispensing will be daily, whether the dose times are scheduled or not, and 100% compliance is assumed.

Rules for scheduled (advance) doses: Rules with respect to scheduling advance doses include existing rules, where a given dose for a specific date cannot be dispensed more than once, and additionally, any scheduled auto dose for a given dose for a specific date will only he scheduled once, so long as it is not already dispensed. It will not be scheduled at all, if already dispensed.

Scheduled advance doses exist silently in the background and auto-dispense as appropriate. Scheduled advance doses are not marked as dispensed until dispense actually occurs, whereas immediate dispenses (Dispense now) will be marked as dispensed, respectively. Thus, the e-MAR will be populated with an entry that the medication dose was vended for the Dispense now doses.

Doses scheduled by the ADS use the inventory at the time of the scheduling. When inventory changes afterward, and affects scheduled advance doses, the respective doses are cancelled. The network is updated with cancelled doses due to inventory effect. The circumstances under which this situation might occur cannot be predicted. However, the scheduling engine will consider inventory levels periodically and assess the impact on scheduled advance doses. If a scheduled advance dose does not dispense, the ADS will not attempt to dispense again. In the rare case where no dose is dispensed, the remote dispense from the network console 26 or local action may be taken to fulfill the dispense if possible.

Dose Schedule Changes: Occasionally, schedules change. When, this happens, existing scheduled advance doses must be considered. if the dose times remain the same, the existing scheduled advance doses can be updated with the respective doses for the new schedule. However, if the dose times change, then all existing scheduled advance doses must be cancelled. If cancellation is determined, the user will be prompted to acknowledge that currently scheduled advance doses will be cancelled in the load screen.

Network console: FIG. 5 shows a user interface display screen that is accessible at the network console 26. if the user has sufficient rights, the network console 26 displays information about advance dose scheduling for each patient, and provides a facility to update the information. Within the detail screen, a new section displays scheduled advance doses. The list displays all scheduled doses within the selected date range. This includes scheduled items in the past, present, and future, dispensed, cancelled, or queued. If a dose time for a given date is scheduled, cancelled and scheduled again, then it will display multiple times. Each time a dose time for a particular date is scheduled, a new record is created. When cancelled, the same record is updated with a cancel flag, but a new record is not created. In the example described, the particular dose time would be displayed two times.

Figure 6:
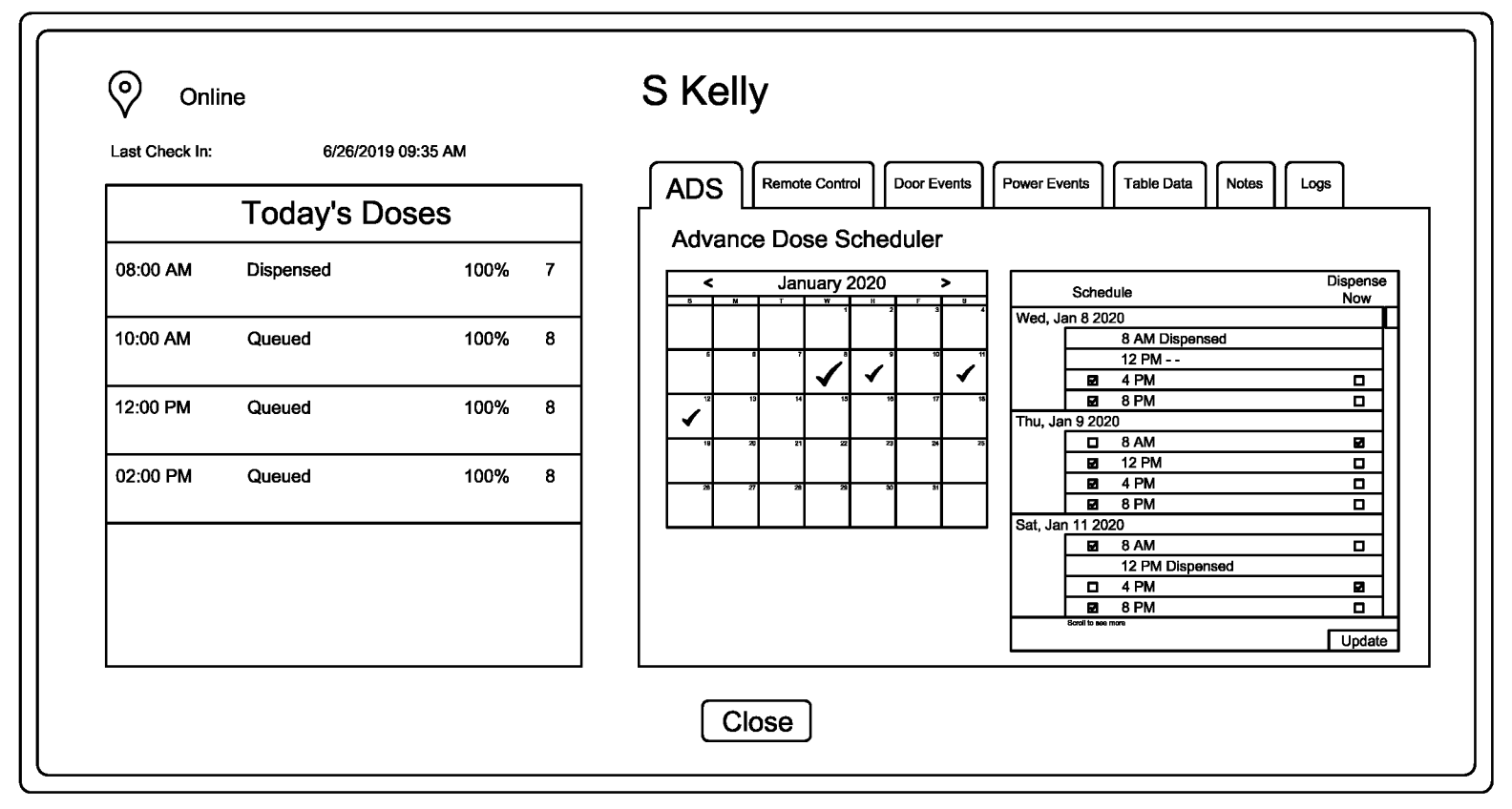

To update, the user selects Edit. The tools work similarly to the device UI tools where the calendar displays check marks fbr selected days, and a list to the right detailing the dose times grouped by date, with check marks indicating schedule status. See the example in FIG. 6.

When updating, the rules use the network version of inventory, subject to local inventory when applied locally. Any discrepancies are updated on the network after the synchronization cycle is complete. The user will need to refresh to pick up any feedback changes that result from discrepancy.

Table data structure for medication vending device 10:
Table to hold the advance dose schedules:
advance_dose_schedules
  _id
  create_date
  create_user
  dose_id
  dose_date
  cancel_date
  cancel_user
  remote_id
  synchronized
Table data structure for network console 26:
Tables to hold the remote control advance dose schedule:
advance_dose_schedules_pending
  _id
  create_date
  create_user
  dose_id
  dose_date
  cancel_date
  cancel_user
  picked_up
  ads_id
advance_dose_schedules
  _id
  create_date
  create_user
  device_id
  dose_id
  dose_date
  cancel_date
  cancel_user
  remote_id
  other_id The Appendix shows source code snippets for implementing one preferred embodiment of the different vending mode.

The present invention may be implemented with any combination of hardware and software. If implemented as a computer-implemented apparatus, the present invention is implemented using means for performing all of the steps and functions described above.

When implemented in software, the software code for the controller 18, and the corresponding programming elements that execute in a processor of the network console 26, can be executed on any suitable processor or collection of processors, whether provided in a single computer or distributed among multiple computers.

The present invention can also be included in an article of manufacture (e.g., one or more non-transitory, tangible computer program products) having, for instance, computer readable storage media. The storage media has computer readable program code stored therein that is encoded with instructions for execution by a processor (here, the controller 18, and the corresponding programming elements that execute in a processor of the network console 26) for providing and facilitating the mechanisms of the present invention. The article of manufacture can be included as part of a computer system or sold separately.

The storage media can be any known media, such as computer memory, one or more floppy discs, compact discs, optical discs, magnetic tapes, flash memories, circuit configurations in Field Programmable Gate Arrays or other semiconductor devices, or other tangible computer storage medium. The storage media can he transportable, such that the, program or programs stored thereon can be loaded onto one or more different computers or other processors to implement various aspects of the present invention as discussed above. The storage media may also be implemented via network storage architecture, wherein many devices, which, are paired together, are available to a network.

The computer(s) used herein for the controller 18 and the network console 26 may be embodied in any of a number of forms, such as a tablet computer. Additionally, a computer may be embedded in a device not generally regarded as a computer but with suitable processing capabilities, including a Personal Digital Assistant (PDA), a smart phone or any other suitable portable, mobile, or fixed electronic device.

The controller 18 and the network console 26 are not a general-purpose computers, but instead are specialized computer machines that perform a myriad of functions (e.g., setting vending modes for the dosing schedule) that are not native to a general-purpose computer, absent the addition of specialized programming.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. The computer program need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, and the like, that perform particular tasks or implement particular abstract data types. The functionality of the program modules may be combined or distributed as desired in various embodiments.

Data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags, or other mechanisms that establish relationship between data elements.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. A medication vending device that is programmed with a dosing schedule for a patient that allows for a plurality of vending modes for different doses and dose times of the dosing schedule, the medication vending device being associated with the patient, the medication vending device comprising:
   (a) a memory that maintains the dosing schedule for the patient associated with the medication vending device, the dosing schedule including:
      (i) a plurality of dose times per day, each day including a fixed number of dose times, and
      (ii) medications that are scheduled to be vended at each dose time; and
   (b) a controller configured to program each dose time with a respective vending mode, the vending modes including:
      (i) a first vending mode configured to cause the medication vending device to output a prompt at the respective dose time indicated by the dosing schedule maintained in the memory, the prompt communicating to the patient that a dose of medication should be vended from the medication vending device by the patient and immediately consumed;
      (ii) a second vending mode configured to cause the medication vending device to automatically vend a dose of medication from the medication vending device at the respective dose time indicated by the dosing schedule maintained in the memory without requiring any action by the patient, wherein the second vending mode is configured to allow for:
         (A) selection of a daily dose time from the plurality of daily dose times indicated by the dosing schedule maintained in the memory, and
         (B) selection of a future date, so as to cause automatic vending of the medication dose for the selected daily dose time indicated by the dosing schedule maintained in the memory for the selected future date without requiring any action by the patient; and
      (iii) a third vending mode configured to cause the medication vending device to immediately vend a dose of medication from the medication vending device without requiring any action by the patient, wherein the third vending mode is configured to allow for:
         (A) selection of a daily dose time from the plurality of daily dose times indicated by the dosing schedule maintained in the memory, and (B) selection of one or more future dates, so as to cause immediate vending of the medication doses for the selected daily dose time indicated by the dosing schedule maintained in the memory for the selected one or more future dates, wherein the controller causes the medication vending device to vend each dose time indicated by the dosing schedule maintained in the memory in accordance with its respective programmed vending mode.

2. The medication vending device of claim 1 wherein the third vending mode is configured to allow for:
   (A) selection of a daily dose time indicated by the dosing schedule maintained in the memory from the plurality of daily dose times, and
   (B) selection of a plurality of future dates, so as to cause immediate vending of the medication doses for the selected daily dose time indicated by the dosing schedule maintained in the memory for the selected plurality of future dates.

3. The medication vending device of claim 2 wherein the plurality of future dates are consecutive future dates.

4. The medication vending device of claim 1 wherein the third vending mode is configured to allow for:
   (A) selection of only one of the daily dose times indicated by the dosing schedule maintained in the memory from the plurality of daily dose times, and
   (B) selection of one or more future dates, so as to cause immediate vending of the medication doses for the one selected daily dose time indicated by the dosing schedule maintained in the memory for the selected one or more future dates.

5. The medication vending device of claim 1 wherein the first vending mode is a default vending mode.

6. The medication vending device of claim 1 wherein the second vending mode is further configured to cause the medication vending device to communicate to the patient that the automatically vended dose of medication vended from the medication vending device should be immediately consumed.

7. The medication vending device of claim 1 wherein the controller receives instructions for programming each dose time with a respective vending mode from a device external to the medication vending device.

8. A computer program product for automatically programming a medication vending device associated with a patient with a dosing schedule that allows for a plurality of vending modes for different doses and dose times of the dosing schedule, the medication vending device being associated with a patient, the computer program product comprising a computer readable medium tangibly embodying non-transitory computer-executable program instructions thereon that, when executed, causes a computing device to:
   (a) maintain in a memory the dosing schedule for the patient associated with the medication vending device, the dosing schedule including:
      (i) a plurality of dose times per day, each day including a fixed number of dose times, and
      (ii) medications that are scheduled to be vended at each dose time; and
   (b) program, using a controller of the medication vending device, each dose time with a respective vending mode, the vending modes including:
      (i) a first vending mode configured to cause the medication vending device to output a prompt at the respective dose time indicated by the dosing schedule maintained in the memory, the prompt communicating to the patient that a dose of medication should be vended from the medication vending device by the patient and immediately consumed;
      (ii) a second vending mode configured to cause the medication vending device to automatically vend a dose of medication from the medication vending device at the respective dose time indicated by the dosing schedule maintained in the memory without requiring any action by the patient, wherein the second vending mode is configured to allow for:
         (A) selection of a daily dose time from the plurality of daily dose times indicated by the dosing schedule maintained in the memory, and
         (B) selection of a future date, so as to cause automatic vending of the medication doses for the selected daily dose time indicated by the dosing schedule maintained in the memory for the selected future date without requiring any action by the patient; and
      (iii) a third vending mode configured to cause the medication vending device to immediately vend a dose of medication from the medication vending device without requiring any action by the patient, wherein the third vending mode is configured to allow for:
         (A) selection of a daily dose time from the plurality of daily dose times indicated by the dosing schedule maintained in the memory, and
         (B) selection of one or more future dates, so as to cause immediate vending of the medication doses for the selected daily dose time indicated by the dosing schedule maintained in the memory for the selected one or more future dates,
   wherein the controller causes the medication vending device to vend each dose time indicated by the dosing schedule maintained in the memory in accordance with its respective programmed vending mode.

9. The computer program product of claim 8 wherein the third vending mode is configured to allow for:
   (A) selection of a daily dose time indicated by the dosing schedule maintained in the memory from the plurality of daily dose times, and
   (B) selection of a plurality of future dates, so as to cause immediate vending of the medication doses for the selected daily dose time indicated by the dosing schedule maintained in the memory for the selected plurality of future dates.

10. The computer program product of claim 9 wherein the plurality of future dates are consecutive future dates.

11. The computer program product of claim 8 wherein the third vending mode is configured to allow for:
   (A) selection of only one of the daily dose times indicated by the dosing schedule maintained in the memory from the plurality of daily dose times, and
   (B) selection of one or more future dates, so as to cause immediate vending of the medication doses for the one selected daily dose time indicated by the dosing schedule maintained in the memory for the selected one or more future dates.

12. The computer program product of claim 8 wherein the first vending mode is a default vending mode.

13. The computer program product of claim 8 wherein the second vending mode is further configured to cause the medication vending device to communicate to the patient that the automatically vended dose of medication vended from the medication vending device should be immediately consumed.

14. The computer program product of claim 8 wherein the controller receives instructions for programming each dose time with a respective vending mode from a device external to the medication vending device.

* * * * *